United States Patent [19]

Siri

[11] Plant 4,907

[45] Oct. 26, 1982

[54] MINIATURE CARNATION

[76] Inventor: Angelo J. Siri, 825 Woolsey St., San Francisco, Calif. 94134

[21] Appl. No.: 232,893

[22] Filed: Feb. 9, 1981

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation sport of Rainbow having lavender and pink blooms.

5 Drawing Figures

BACKGROUND OF THE NEW PLANT

This invention comprises a new and distinct miniature carnation variety that has its own set of characteristics that set it apart from all other varieties of miniature carnations. The newly discovered variety, called "Rainbow," originated as a sport of Petite Purple a patented variety, U.S. Plant Pat. No. 3,767.

The botanical classification of the new variety is *Dianthus caryophyllus longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
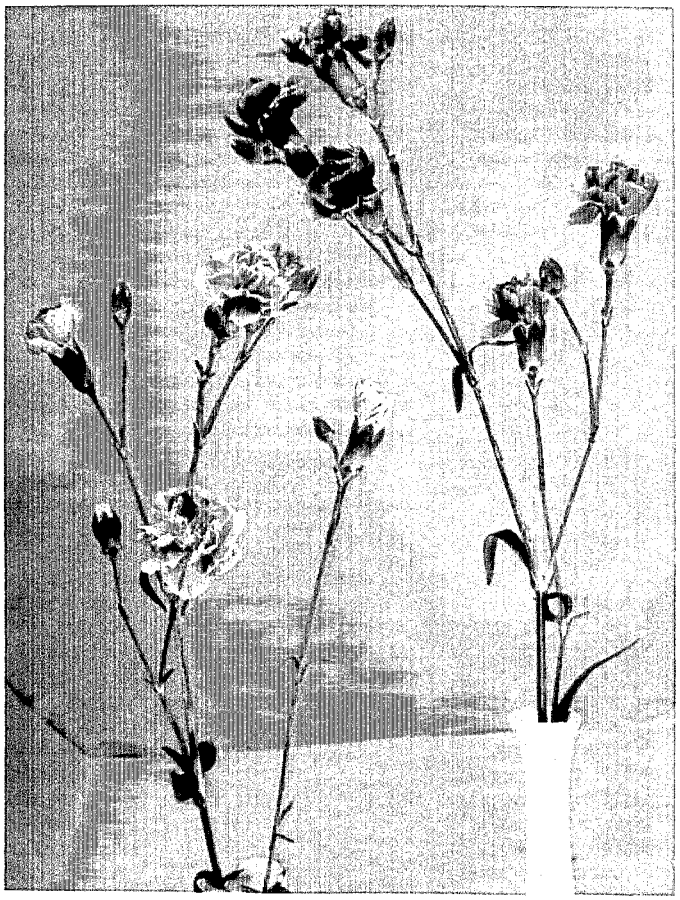
FIG. 1. PRIOR ART
FIG. 1 shows on the left a spray of the new variety "Rainbow," and on the right a spray of the prior Petite Purple.
Figure 2:
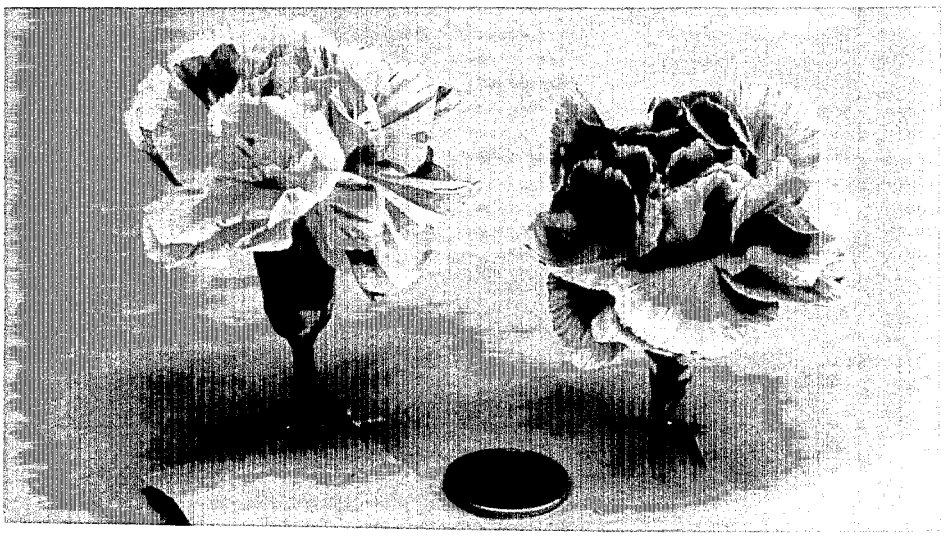
FIG. 2. PRIOR ART
FIG. 2 shows enlarged views of the flowers, Rainbow on the left and Petite Purple on the right.
Figure 3:
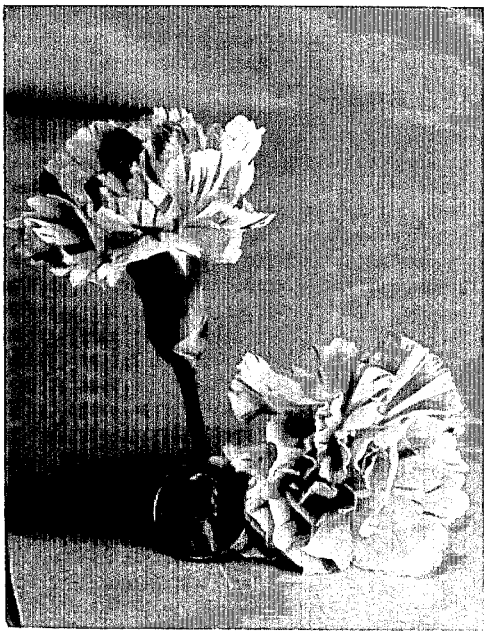
FIG. 3 shows another view of the new variety Rainbow flower.
Figure 4A:
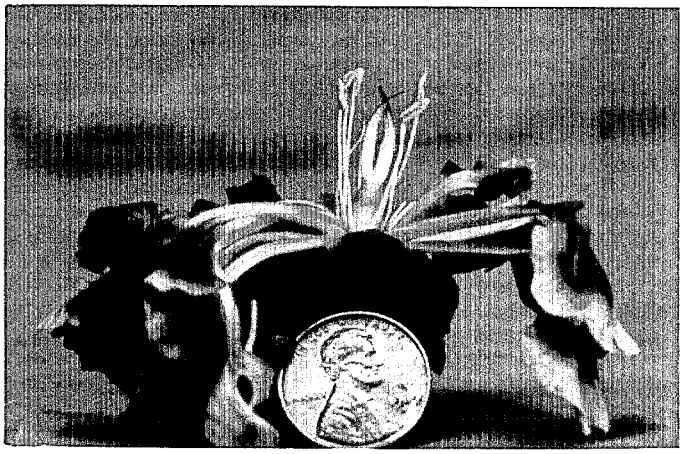
FIG. 4A. PRIOR ART
FIG. 4A is an enlarged view of the prior Petite Purple flower opened to expose the stamen and pistils.
Figure 4B:
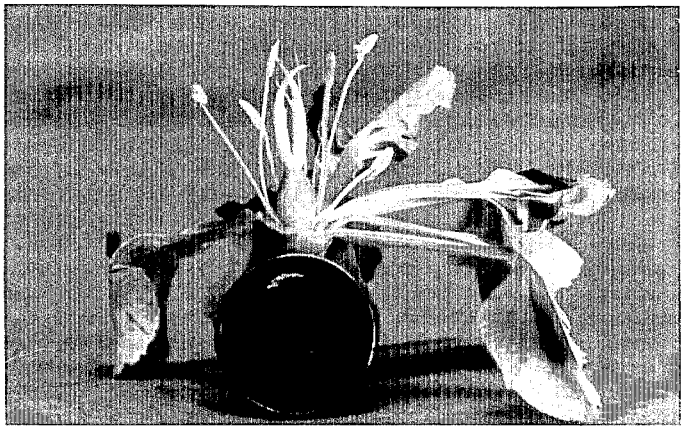
FIG. 4B is an enlarged view of the new variety Rainbow flower opened to expose the stamen and pistils.

The following detailed description of the new variety is based on my detailed observations of the new cultivar which were made at Siri Brothers Nursery Inc. at 940 O'Connor St., East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore Md. and "RHS" for Royal Horticultural Color Chart, Royal Horticultural Society, London, England.

GROWTH HABITS

Height: Short to medium.
Foliage: Average.
Speed of growth: Fast.
Root system: Average.

FOLIAGE

Leaf size:

*Length varies.*—Longer at the bottom of stem, shorter at the top. Average at the middle of the stem 3½ inches.

*Width varies.*—Wider at the bottom of stem, shorter at the top. Average at the middle of the stem ⅜ inches.

*Features.*—There is a little mottling on the leaves.

Leaf shape: Very little curl with a long acuminating tip.
Leaf texture: Smooth and leathery.
Leaf color:

*Upperside.*—RHS Greengroup 139A with a whitish color over the green.

*Underside.*—Same as upperside.

Leaf ribs: One rib down the center from the base to the tip of the leaf.
Leaf habit: Very little curl.
Leaf density: Average.

STEM

Stem strength: Average.
Stem color: RHS Greengroup 139A with a whitish color over the green.
Nodes: Average; space between nodes 3½ inch average at midstem.
Stem branching: Very good, wide gaps between the branches, not clubby.

BUDS

Bud shape: Oval.
Bud color: Top half of bud LCC H-21 L-13 . Bottom half blends into LCC H-22 L-9.
Average number of flowering buds per stem: 4 to 5.
Uniformity of bud opening: Very uniform.
Bud splitting: Very seldom.
Number of sepals per calyx: 65% of calyxs have 5, 26% of calyxs have 6, and 9% of calyxs have 7.

FLOWER

Description of the color of the bloom: The bloom is a hot pink color (LCC H-40 L-6) with a light lavender that appears white, fringe (LCC H-48 L-1) and deep lavender blotches and stripes of varying size running from the base of the bloom to the outer edge (LCC H-43 L-14).

General tonality of the color: Bright.

Diameter of average bloom: $2\frac{1}{4}''$ to $3''$.

Bloom shape: Generally round with a high center and flat outer petals.

Keeping quality: Average.

Fragrance: Slight.

PETALAGE

Petal texture: Soft and velvety

Petal edge: Medium to slight serration.

Petal color: (Note: interspersal of colors — most petals are pink with varying amounts of lavender interspersed. However, some petals are mostly lavender with varying amounts of pink interspersed. Most but not all petals have a light lavender edging. The pink and lavender run into this light lavender. The bloom is a montage of these colors in blotches and stripes. The pink, lavender, and light lavender are random on the petal. There is no exact set pattern although there is a consistent one.

*Topside base of petal.*—Pink LCC H-40 L-6, Lavender LCC H-43 L-14.

*Topside middle of petal.*—Pink LCC H-40 L-6, Lavender LCC H-43 L-14.

*Topside outside of petal.*—Light Lavender LCC H-48 L-1 and Lavender LCC H-43 L-4.

*Underside base of petal.*—Pink LCC H-40 L-5, Lavender LCC H-43 L-13.

*Underside middle of petal.*—Pink LCC H-40 L-5, Lavender LCC H-43 L-13.

*Underside outside of petal.*—Light Lavender LCC H-48 L-1 and Lavender LCC H-43 L-13.

Color stability: Excellent. There is approximately a 1% reversion to Petite Purple U.S. Plant Pat. No. 3,767.

Petal size:

*Average length.*—$1\frac{7}{8}$ inches.

*Average width.*—At widest point $\frac{7}{8}$ inches.

Calyx color: Top half LCC H-21 L-13, bottom half blends into LCC H-22 L-9, tips of leaves on the bottom of calyx LCC H-22 L-15.

REPRODUCTIVE ORGANS

Stamen: With anthers.

Average length of stamen: 1 inch.

Color of anthers: The background is LCC H-26 L-1 with varying shades of lavender specks about the color LCC H-44 L-8.

Color of filament: LCC H-39 L-1.

Pistils:

*Shape.*—Approximately 80% have 2 styles, 10% have 1 style and 10% have 3 styles.

*Number.*—One.

*Length from tip to ovary.*—Approximately $\frac{7}{8}$ inch.

Stigma:

*Shape.*—Round.

*Color.*—White. It is located at the very tip of the style.

Style:

*Color.*—Bottom LCC H-25 L-1, toward tip LCC H-43 L-14.

Ovary:

*Shape.*—Ovid.

*Color.*—Top half LCC H-22 L-4, bottom half LCC H-23 L-2.

*Length.*—Approximately $\frac{3}{8}$ inch.

*Width.*—Approximately 3/16 inch.

DISTINGUISHING CHARACTERISTICS BETWEEN THE NEW VARIETY AND PARENT

The most obvious distinguishing characteristic is the color of the bloom. It is pink with lavender stripes and a light lavender fringe. In contrast, Petite Purple, the parent, is a deep purple with light lavender fringe.

The styles of the parent, Petite Purple, have much more of the lavender color LCC H-43 L-14 than do the styles of Rainbow. The color is much more intense and covers more of the style in Petite Purple.

The anthers of the parent, Petite Purple, are a very distinctly different color. They are much more lavender than Rainbow. The color of Petite Purple's anthers is LCC H-48 L-8. The color of Rainbow's anthers is LCC H-26 L-1 — the background, and LCC H-44 L-8 — the specks. Petite Purple's anthers do not have specks.

SIMILAR CHARACTERISTICS OF THE NEW VARIETY AND PARENT

All of the characteristics of both varieties are similar except for the distinguishing characteristics referred to above.

I claim:

1. A new and distinct variety of miniature carnation plant, substantially as herein shown and described.

* * * * *